US012409302B2

(12) United States Patent
Lackey et al.

(10) Patent No.: US 12,409,302 B2
(45) Date of Patent: Sep. 9, 2025

(54) CATHETER POSITION INDICATOR AND RELATED SYSTEMS AND METHOD

(71) Applicant: Becton, Dickinson and Company, Franklin Lakes, NJ (US)

(72) Inventors: John Lackey, West Valley City, UT (US); Yiping Ma, Layton, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 280 days.

(21) Appl. No.: 17/362,606

(22) Filed: Jun. 29, 2021

(65) Prior Publication Data

US 2022/0023591 A1    Jan. 27, 2022

Related U.S. Application Data

(60) Provisional application No. 63/055,210, filed on Jul. 22, 2020.

(51) Int. Cl.
*A61M 25/01*    (2006.01)
*A61M 25/00*    (2006.01)
*A61M 25/06*    (2006.01)

(52) U.S. Cl.
CPC .... *A61M 25/0105* (2013.01); *A61M 25/0612* (2013.01); *A61M 2025/0008* (2013.01); *A61M 2205/18* (2013.01)

(58) Field of Classification Search
CPC ...... A61M 2025/0008; A61M 25/0105; A61M 2025/0166; A61M 25/0108; A61M 2205/584; A61M 25/0606; A61M 2025/0681; A61M 5/158; A61M 25/0662; A61M 25/06; A61M 25/0612; A61M 25/00; A61M 29/00; A61M 25/065; A61M 2205/583; A61M 2205/18; A61M 2210/12; A61B 2090/0807; A61B 2090/0811; A61B 17/3417; A61B 2090/062; A61B 2090/3937; A61B 2017/00455; A61B 2090/3966
See application file for complete search history.

(56) References Cited

U.S. PATENT DOCUMENTS

2003/0153874 A1* 8/2003 Tal .................. A61M 25/0606
2004/0111059 A1   6/2004 Howlett et al.
(Continued)

FOREIGN PATENT DOCUMENTS

AT    474500 T       8/2010
AU    2005317124     6/2006
(Continued)

*Primary Examiner* — Michael J Tsai
*Assistant Examiner* — Kathleen Paige Farrell
(74) *Attorney, Agent, or Firm* — Kirton McConkie; Whitney Blair; Kevin Stinger (57) ABSTRACT

A catheter assembly may include a catheter adapter having a catheter extending from its distal end. The catheter may include a proximal end, a tip, and a length of tubing therebetween. The length of tubing may include one or more position indicators to indicate a position of the catheter relative to a vasculature. The catheter assembly may include an introducer needle extending through the length of tubing and comprising a sharp distal tip configured to introduce the catheter into the vasculature.

14 Claims, 4 Drawing Sheets

(56) References Cited

U.S. PATENT DOCUMENTS

| | | |
|---|---|---|
| 2006/0074352 A1 | 4/2006 | Case |
| 2006/0149165 A1 | 7/2006 | Kennedy et al. |
| 2009/0162530 A1* | 6/2009 | Nesbitt ......... A61M 2025/0008 604/265 |
| 2009/0187153 A1* | 7/2009 | West et al. ............. A61B 5/153 |
| 2009/0192496 A1 | 7/2009 | Suwito et al. |
| 2011/0054456 A1* | 3/2011 | Thompson ......... A61B 18/1492 606/29 |
| 2012/0296275 A1 | 11/2012 | Martin et al. |
| 2013/0006178 A1 | 1/2013 | Pinho et al. |
| 2014/0058251 A1* | 2/2014 | Stigall ...................... A61B 6/12 600/407 |
| 2014/0121643 A1* | 5/2014 | McKinnis ............. A61F 2/0105 604/528 |
| 2017/0281142 A1 | 10/2017 | Martin et al. |
| 2017/0296798 A1* | 10/2017 | Kume ............... A61M 25/0068 |
| 2018/0071497 A1* | 3/2018 | Hurley .................. A61M 19/00 |
| 2019/0117938 A1* | 4/2019 | Norman ............ A61M 25/0045 |
| 2019/0374748 A1* | 12/2019 | Isaacson ........... A61M 25/0606 |
| 2020/0038628 A1* | 2/2020 | Chou .................... A61M 25/01 |
| 2021/0045723 A1 | 2/2021 | Martin et al. |

FOREIGN PATENT DOCUMENTS

| | | |
|---|---|---|
| AU | 2019281727 A1 | 1/2021 |
| BR | 112020024567 A2 | 3/2021 |
| CA | 2590001 A1 | 6/2006 |
| CA | 3101744 A1 | 12/2019 |
| CN | 102846308 A | 1/2013 |
| CN | 105193479 B | 12/2017 |
| CN | 112272572 A | 1/2021 |
| DE | 102013101538 B3 | 7/2014 |
| DE | 102016112598 A1 | 1/2018 |
| EP | 1830706 A1 | 9/2007 |
| EP | 2244780 A1 | 11/2010 |
| EP | 2540214 A1 | 1/2013 |
| EP | 2709712 A2 | 3/2014 |
| EP | 2956071 A1 | 12/2015 |
| EP | 3801728 A1 | 4/2021 |
| ES | 2391004 T3 | 11/2012 |
| ES | 2723792 T3 | 9/2019 |
| JP | H11347130 A | 12/1999 |
| JP | 2008523908 A | 7/2008 |
| JP | 2011510744 A | 4/2011 |
| JP | 2013009949 A | 1/2013 |
| JP | 5503554 B2 | 5/2014 |
| JP | 2015181671 A | 10/2015 |
| JP | 6054056 B2 | 12/2016 |
| JP | 2021526893 A | 10/2021 |
| KR | 20210018410 A | 2/2021 |
| SG | 11202011463X | 12/2020 |
| WO | 2006041971 A1 | 4/2006 |
| WO | 2006065909 A1 | 6/2006 |
| WO | 2009097289 A1 | 8/2009 |
| WO | 2012156819 A2 | 11/2012 |
| WO | 2014124719 A1 | 8/2014 |
| WO | 2019236248 A1 | 12/2019 |

\* cited by examiner

CATHETER POSITION INDICATOR AND RELATED SYSTEMS AND METHOD

RELATED APPLICATIONS

This application claims benefit of U.S. Provisional Patent Application No. 63/055,210, filed on Jul. 22, 2020, entitled CATHETER POSITION INDICATOR AND RELATED SYSTEMS AND METHODS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing away from skin of the patient. The catheter and the introducer needle are generally inserted at a shallow angle through the skin into vein of the patient.

In order to verify proper placement of the introducer needle and/or the catheter in the blood vessel, a clinician generally confirms that there is blood "flashback." Thus, the clinician may visualize the blood and thereby confirm placement of the introducer needle within the vasculature. Once placement of the needle has been confirmed, the clinician may temporarily occlude flow in the vein and remove the introducer needle, leaving the catheter in place and secured for future blood withdrawal and/or fluid infusion.

In some cases, however, the catheter may become displaced or "dislodged" due to improper securement or, more commonly, due to forces that are greater than the securement method was designed to withstand. For example, catheter dislodgement may occur when a patient rolls over in bed, catches their line on a bed rail, transfers between beds, fidgets, or intentionally pulls out their line.

At minimum, catheter dislodgement may necessitate a restart of the intravenous catheter, which places clinicians at an increased risk due to potential sharps injuries as well as blood or drug exposure. In addition, an intravenous catheter restart may be both inconvenient and uncomfortable for the patient. In more serious cases, such as where dislodgement causes loss of peripheral intravenous site integrity, the patient may need to be fit with a more invasive central line with increased risks of phlebitis, infiltration, and infection, as well as longer treatment times. Potential worst-case scenarios may include bleed outs, air embolisms, and bloodstream infections and associated risks of patient death.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods. As previously discussed, dislodgement may occur due to improper securement or, more commonly, dislodgement caused from patients rolling over in bed, catching their lines on bed rails, transferring to a different bed, fidgeting, or intentionally pulling on their lines, for example.

Such dislodgement may necessitate a line restart, which tends to be both inconvenient and uncomfortable. In some cases, the patient may need to be fit with a more invasive central line, associated with increased risks of phlebitis, infiltration, infection, as well as longer treatment times. Worst-case scenarios may include bleed outs, air embolisms, and bloodstream infections with increased risk of patient death. Embodiments described herein may provide an early indication of catheter movement to thereby reduce a risk of dislodgement and its associated complications.

In some embodiments, a catheter assembly may include a catheter adapter having a proximal end, a distal end, and a lumen extending therebetween. In some embodiments, a catheter may extend from the distal end. In some embodiments, the catheter may include a proximal end, a tip, and a length of tubing therebetween. In some embodiments, the length of tubing may include at least one position indicator to indicate a position of the catheter relative to a vasculature of a patient.

Some embodiments may include an introducer needle extending through the length of tubing. In some embodiments, the introducer needle may include a sharp distal tip configured to introduce the catheter into the vasculature.

In some embodiments, the at least one position indicator may include at least one marking disposed on an outer surface of the length of tubing. Some embodiments of the at least one marking may include a colored band, a tick mark, or a graduated mark. In some embodiments, the at least one marking comprises a plurality of non-uniformly spaced markings. In other embodiments, the at least one marking comprises a plurality of uniformly spaced markings.

In some embodiments, a distance between non-uniformly spaced markings may decrease proximate to the distal end of the catheter adapter. In some embodiments, the at least one marking may indicate a distance to the distal end of the catheter. In some embodiments, the at least one marking may indicate dislodgement of the catheter relative to the vasculature. Some embodiments of the at least one position indicator may include a first position indicator located near the tip of the catheter and a second position indicator located near the proximal end of the catheter.

In some embodiments, a vascular access device to detect a catheter position within a vasculature may include a catheter comprising a proximal end, a tip, and a length of tubing therebetween. In some embodiments, a position indicator may be disposed on an outer surface of the length of tubing and may be configured to indicate a position of the catheter within a vasculature.

In some embodiments, the position indicator may include at least one marking printed onto the outer surface of the length of tubing. In some embodiments, the position indicator may include a plurality of markings. In some embodiments, each of the plurality of markings is uniformly spaced.

In some embodiments, each of the plurality of markings may include a non-uniform characteristic. The non-uniform characteristic may include, for example, color, width, length, and/or spacing. In some embodiments, the position indicator may be a colored band, a tick mark, or a graduated mark.

In some embodiments, the position indicator may include a first plurality of markings located near the tip of the catheter and a second plurality of markings located near the proximal end of the catheter. In some embodiments, each of the first plurality of markings may be uniformly spaced from each other of the first plurality of markings. Likewise, each of the second plurality of markings may be is uniformly spaced from each other of the second plurality of markings.

Some embodiments may include a method for detecting catheter position. In some embodiments, the method may include providing a catheter assembly to introduce a catheter into a vasculature of a patient. Some embodiments of the catheter assembly may include a catheter adapter comprising a proximal end, a distal end, and a lumen extending therebetween. The catheter may extend from the distal end. In some embodiments, the catheter may include a proximal end, a tip, and a length of tubing therebetween. Some embodiments of the length of tubing may include a position indicator to indicate a position of the catheter relative to the vasculature.

In some embodiments, an introducer needle may extend through the length of tubing. Some embodiments of the introducer needle may include a sharp distal tip to introduce the catheter into the vasculature at an intravenous entry site of the patient. In some embodiments, the catheter may be secured such that the position indicator is aligned with the intravenous entry site. Some embodiments of the method may further include automatically monitoring a location of the position indicator relative to the intravenous entry site to detect catheter dislodgement.

In some embodiments, the position indicator may include a plurality of markings printed onto an outer surface of the length of tubing. In some embodiments, the method may further include automatically activating an alert in response to the location of the position indicator misaligning with the intravenous entry site.

It is to be understood that both the foregoing general description and the following detailed description are exemplary and explanatory and are not restrictive of the present disclosure, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

As used in this specification, the term "distal" refers to a direction away from a clinician who would place the device into contact with a patient, and nearer to the patient. The term "proximal" refers to a direction nearer to the clinician who would place the device into contact with the patient, and farther away from the patient. Thus, for example, the end of a catheter first touching the body of the patient is the distal end, while the opposite end of the catheter is the proximal end of the catheter.

As previously mentioned, the catheter may become dislodged due to improper securement or an intentional or unintentional application of force to the catheter or catheter adapter. For example, catheter dislodgement may occur when a patient rolls over in bed, catches their line on a bed rail, transfers between beds, fidgets, or intentionally pulls out their line.

Catheter dislodgement may necessitate a line restart, placing a clinician at an increased risk due to potential sharps injury as well as exposure to blood and/or drugs. An intravenous catheter restart may also be both inconvenient and uncomfortable for the patient. In more serious cases, such as where dislodgement causes loss of peripheral intravenous site integrity, the patient may need to be fit with a more invasive central line with increased risks of phlebitis, infiltration, and infection, as well as longer treatment times. Potential worst-case scenarios may include bleed outs, air embolisms, and bloodstream infections and associated risks of patient death. Embodiments described herein may provide an early indication of catheter displacement or dislodgement to enable a clinician to immediately address the issue without requiring a line restart.

Figure 1A:
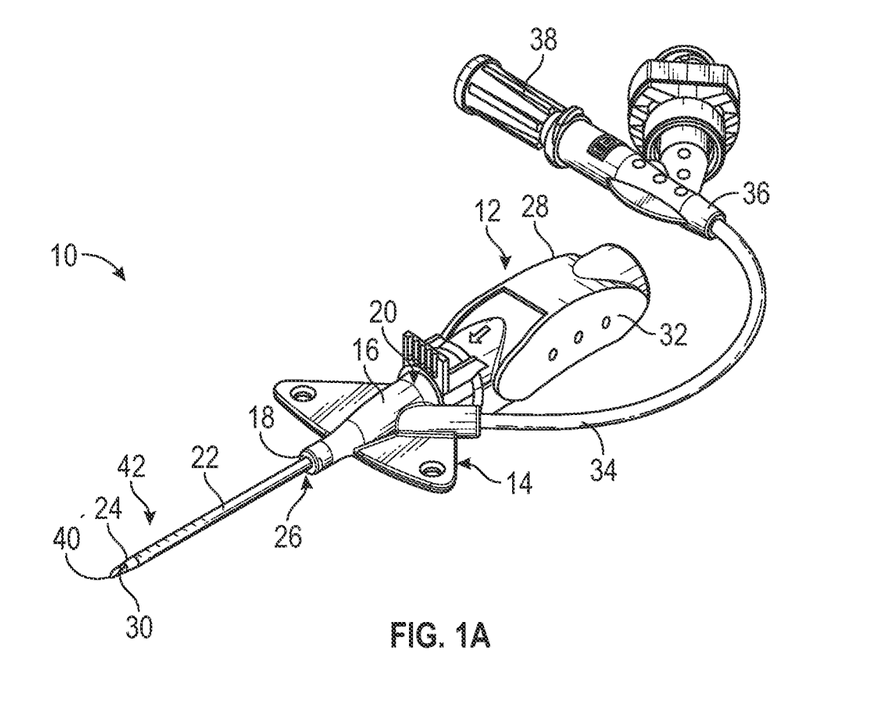
FIG. 1A is an upper perspective view of an example catheter assembly, according to some embodiments.
Figure 1B:
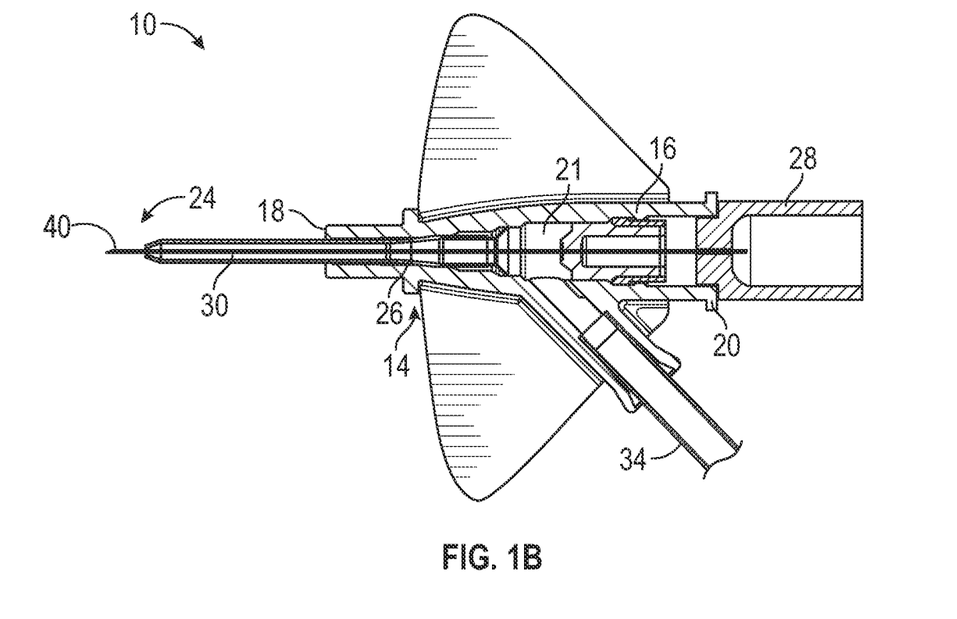
FIG. 1B is a cross-sectional view of the catheter assembly of FIG. 1A, according to some embodiments.

Referring now to FIGS. 1A-1B, in some embodiments, a catheter system 10 may include a needle assembly 12 and a catheter assembly 14. FIGS. 1A-1B illustrate the catheter system in an insertion position, ready for insertion into a vein of a patient, according to some embodiments. In some embodiments, the catheter assembly 14 may include a catheter adapter 16, which may include a distal end 18, a proximal end 20, and a lumen 21 extending therebetween. In some embodiments, the catheter 22 may extend from the distal end 18. Some embodiments of a catheter 22 may include a peripheral intravenous catheter ("PIVC"). In some embodiments, the catheter 22 may include a proximal end 26, a tip 24, and a length of tubing therebetween. In some embodiments, the proximal end 26 of the catheter 22 may be secured within the catheter adapter 16.

In some embodiments, the needle assembly 12 may include a needle hub 28, which may be removably coupled to the catheter adapter 16. In some embodiments, the needle assembly 12 may include an introducer needle 30. In some embodiments, a proximal end of the introducer needle 30 may be secured within the needle hub 28. In some embodiments, the introducer needle 30 may extend through the length of tubing when the catheter 22 is ready for insertion into the vein of a patient, as illustrated, for example, in FIGS. 1A-1B.

In some embodiments, the needle assembly 12 may include a needle grip 32, which a clinician may grip and move proximally to withdraw the introducer needle 30 from the vein once placement of the catheter 22 within the vein is confirmed. In some embodiments, the catheter assembly 14 may include an extension tube 34. In some embodiments, a distal end of the extension tube 34 may be coupled to the catheter adapter 16 and a proximal end of the extension tube 34 may be coupled to an adapter 36.

In some embodiments, a fluid infusion device may be coupled to the adapter 36 to deliver fluid to the patient via the catheter 22 inserted in the vein when the introducer needle 30 is removed from the catheter assembly 14. In some embodiments, a blood collection device may be coupled to the adapter 36 to withdraw blood from the patient via the catheter 22 inserted in the vein.

In some embodiments, the catheter assembly 14 may be an integrated catheter system 10, having the extension tube 34 integrated within the catheter adapter 16 such as, for example, the BD NEXIVA™ Closed IV Catheter System, the BD NEXIVA™ DIFFUSICS™ Closed IV Catheter System, the BD PEGASUS™ Safety Closed IV Catheter System, or another integrated catheter system. An example of an integrated catheter system 10 is illustrated in FIGS. 1A-1B. In some embodiments, the catheter assembly 14 may be non-integrated, without the extension tube 34.

In some embodiments, the catheter assembly 14 may be vented to observe blood and facilitate proximal flow of blood within the introducer needle 30 and/or the catheter 22. In some embodiments, the catheter assembly 14 may be vented in any suitable manner. For example, a vent plug 38 may be coupled to the adapter 36 during insertion of the catheter assembly 14 into the patient. In some embodiments, the vent plug 38 may be permeable to air but not to blood. In some embodiments, the catheter 22, the catheter adapter 16, the extension tube 34, the adapter 36, and the vent plug 38 may be in fluid communication.

In some embodiments, blood may flow through a sharp distal tip 40 of the introducer needle 30 in response to the introducer needle 30 being inserted into a vein of the patient. The blood flow may cause "flashback," or give an indication to the clinician that the introducer needle 30 has entered the vein. After confirming the sharp distal tip 40 is positioned within the vein of the patient, the clinician may lower an insertion angle and advance the catheter 22 a short distance to ensure the distal end 24 of the catheter 22 is in the vein before threading the catheter 22 off the introducer needle 30. The distal end 24 of the catheter 22 may be separated from a proximal end of the sharp distal tip 40 of the introducer needle 30 by a distance called "lie distance." In some embodiments, a length of a bevel extending from the sharp distal tip 40 may vary by gauge size of the introducer needle 30. Accordingly, in some embodiments, a distance the catheter 22 needs to travel from the sharp distal tip 40 to enter the vein may vary by gauge and lie distance. Catheter 22 insertion may fail in the event the catheter 22 is threaded off the introducer needle 30 too soon.

In some embodiments, the length of tubing of the catheter 22 may include a position indicator 42 to indicate a position of the catheter 22 relative to a vasculature of a patient. The position indicator 42 may be one or more markings 44 disposed on an outer surface of the length of tubing. Some embodiments of the one or more markings 44 may include one or more colored bands, tick marks, or graduated marks. In some embodiments, the marking 44 may include a plurality of non-uniformly spaced markings 44. In other embodiments, the marking 44 may include multiple uniformly spaced markings 44.

In some embodiments, the position indicator 42 may include a plurality of markings 44, which may indicate to the clinician a depth of insertion of the catheter 22 into the vein. In some embodiments, the spacing between the markings 44 may be a fraction of the lie distance. In some embodiments, the lie distance may be gauge dependent. In some embodiments, the clinician may advance the catheter 22 several markings 44 before threading off the catheter 22 from the introducer needle 30. In some embodiments, a distance between non-uniformly spaced markings 44 may decrease proximate to the distal end 18 of the catheter adapter 16. In some embodiments, the one or more markings 44 may indicate a distance to the distal end 24 of the catheter 22. In some embodiments, the markings 44 may indicate dislodgement of the catheter 22 relative to the vasculature. Some embodiments of the position indicator 42 may include a first position indicator 42 located near the tip 24 of the catheter 22 and a second position indicator located near the proximal end 26 of the catheter 22. In some embodiments, the first position indicator 42 may include a first plurality of markings 44 uniformly spaced from each other. Likewise, each of the second position indicator 42 may include a second plurality of markings 44 uniformly spaced with respect to each other.

Figure 2:
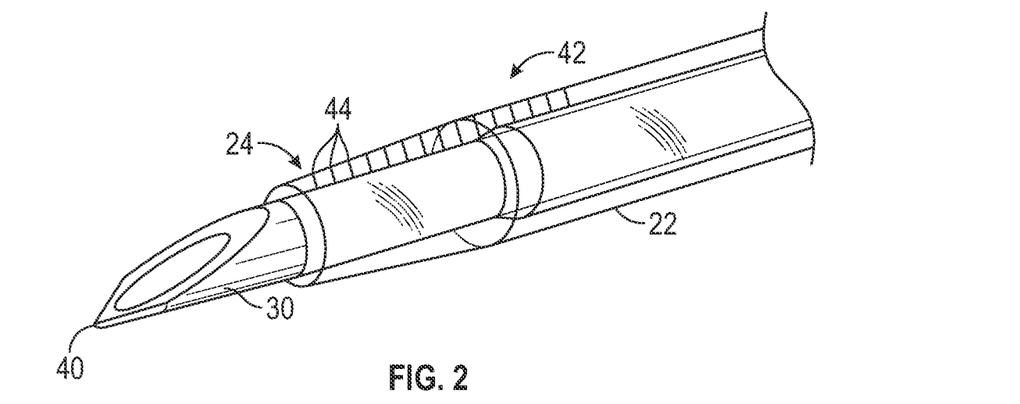
FIG. 2 is an upper perspective view of an example catheter illustrating multiple position indicators according to some embodiments.

Referring now to FIG. 2, in some embodiments, the position indicator 42 may include markings 44 printed on the surface of the length of tubing of the catheter 22. In some embodiments, the position indicator 42 may include patterns or material applied to the surface or bonded to the surface. In some embodiments, the markings 44 may be pad printed or etched onto the length of tubing. In other embodiments, the markings 44 may be applied by any other suitable method such as screen printing, digital printing, flexography printing, UV-Litho printing, or laser printing. In some embodiments, the markings 44 may be printed in several colors or patterns.

In some embodiments, each of the markings 44 may include a non-uniform characteristic. The non-uniform characteristic may include, for example, color, width, length, and/or spacing. In some embodiments, the markings 44 may be staggered or spaced apart in the longitudinal axial direction. In these embodiments, the placement of the markings 44 may facilitate identification by the clinician of a depth at which the tip 24 of the catheter 22 is inserted. In these embodiments, the markings 44 may facilitate confirmation of one or more positions of the catheter tip 24 with respect to the vasculature or surface of skin.

For example, in some embodiments, the markings 44 may indicate that the catheter 22 has entered the vein, that the catheter 22 has been further fed into the vein, and/or that the catheter 22 has been fully inserted into the vein. In some embodiments, the markings 44 may be configured to indicate the tip 24 of the catheter 22 is within the vein. In some embodiments, the markings 44 may be configured to indicate the tip 24 of the catheter 22 is withdrawn or partially withdrawn from the vein. In some embodiments, the markings 44 may facilitate visualization of blood flashback by the clinician, thereby confirming insertion of the introducer needle 30 within the vasculature.

Figure 3A:
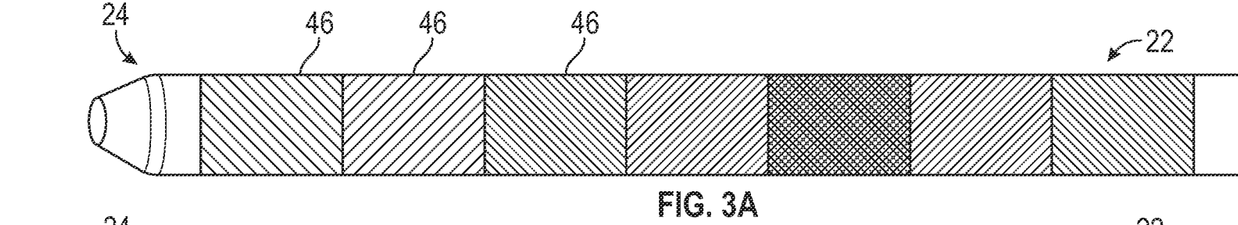
FIG. 3A is an upper perspective view of an example catheter, according to some embodiments.

Referring now to FIG. 3A, in some embodiments, the markings 44 may be colored bands 46. In some embodiments the colored bands 46 may be of uniform width. In other embodiments, the colored bands 46 may be a non-uniform width. Because it is often difficult to determine a position or depth of the catheter 22 at a glance, contrasting colors may be a particularly useful. As the catheter 22 is inserted further into the vasculature or vein, the color that is visible at the surface of the skin may provide a more intuitive indication or reference of the depth of insertion of the catheter 22 into the vein. In some embodiments, the visible color may indicate dislodgement of the catheter 22 after it has been previously positioned and secured, which will be explained in more detail below. In some embodiments, the colors and width of the bands of the position indicator 42 may vary depending on the application of the catheter 22.

Figure 3B:
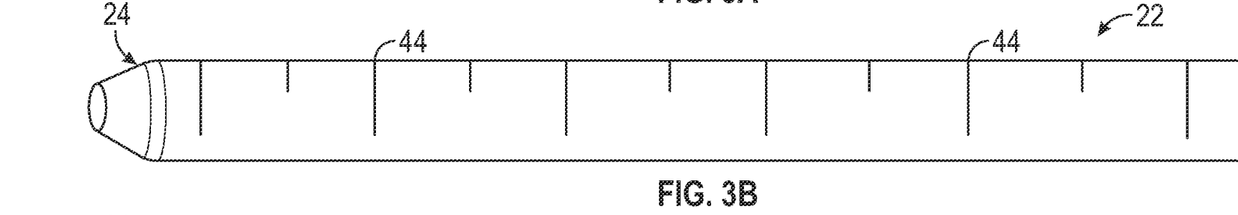
FIG. 3B is an upper perspective view of an example catheter, according to some embodiments.

Referring now to FIG. 3B, in some embodiments, the plurality of markings 44 may be uniform or evenly spaced apart. In some embodiments, the markings 44 may include lines or tick marks 44 generally perpendicular to a longitudinal axis of the catheter 22. In some embodiments, the tick marks 44 may be uniform or may alternate between major and minor tick marks 44 to more accurately indicate the depth of the catheter 22 and help to provide a clear visual reference. In some embodiments, the thickness and spacing of the marks 44 may vary according to the application of the position indicator. In some embodiments, the clinician may insert the catheter 22 such that a particular marking 44 is aligned or even with an outer surface of skin of the patient. In some embodiments, the particular marking 44 or color band 46 may be aligned with skin of the patient to indicate to the clinician that the catheter 22 has been properly inserted into the vasculature or vein.

Figure 3C:
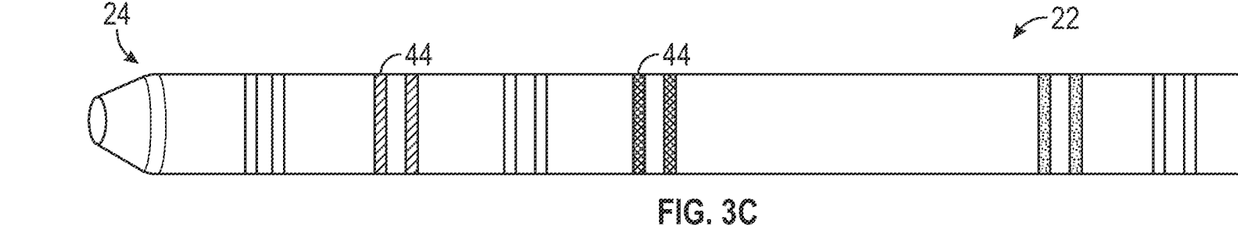
FIG. 3C is an upper perspective view of an example catheter, according to some embodiments.
Figure 3D:
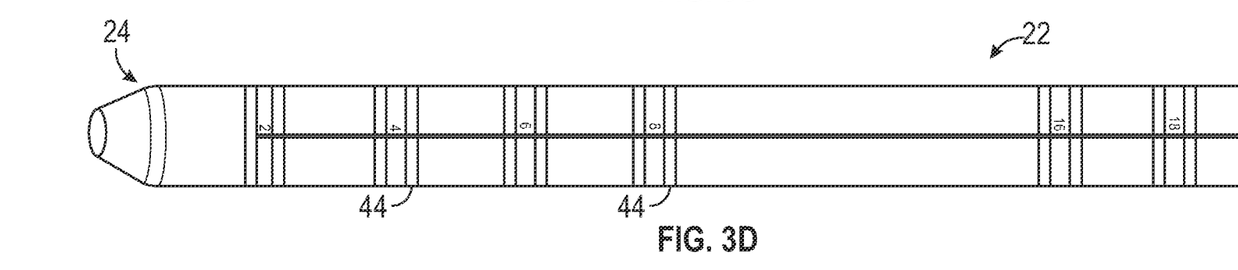
FIG. 3D is an upper perspective view of an example catheter, according to some embodiments.

Referring now to FIGS. 3C and 3D, in some embodiments, the position indicator 42 may include more than one plurality of markings 44. In some embodiments, one or more pluralities of markings 44 may be located near the catheter tip 24. Likewise, in some embodiments, one or more pluralities of markings 44 may be located near the proximal end 26 of the catheter 22. In these and other embodiments, the pluralities of markings 44 may be uniformly or non-uniformly spaced.

Figure 4:
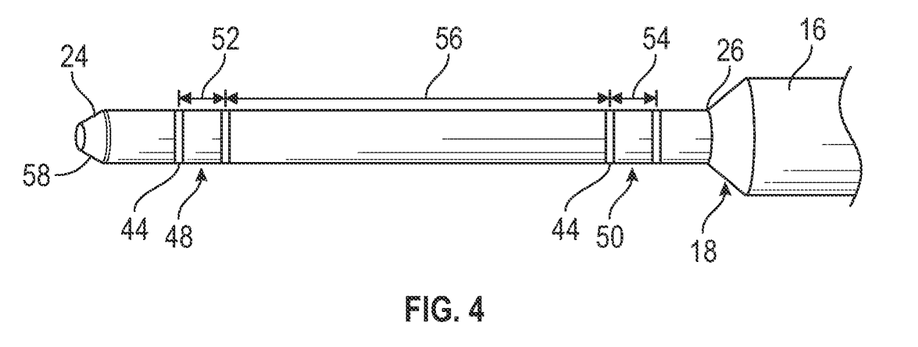
FIG. 4 is an upper perspective view of an example catheter of the catheter assembly of FIG. 1A, according to some embodiments.

Referring now to FIG. 4, in some embodiments, the position indicator 42 may include a first plurality of markings 48 and a second plurality of markings 50. In some embodiments, the first plurality of markings 48 may be located near the catheter tip 24 and the second plurality of markings may be located near the proximal end 26 of the catheter 22. In some embodiments, the first plurality of markings 48 and the second plurality of markings 50 may be uniformly spaced. In other embodiments, the first plurality of markings 48 and the second plurality of markings 50 may be non-uniformly spaced. In at least one embodiment, the first plurality of markings 48 may include two marks 44 spaced apart by a first distance 52. In at least one embodiment, the first distance 52 may be approximately 2-3 mm. The second plurality of markings 50 may also include two marks 44 spaced apart by a second distance 54. In some embodiments, the second distance 54 may also be approximately 2-3 mm. In some embodiments, the first plurality of markings and the second plurality of markings may be spaced apart by a third distance 56. In one embodiment, the third distance 56 may be approximately 5-10 mm.

In some embodiments, the first plurality of markings 48 may provide a reference for depth of insertion of the catheter 22 and the second plurality of markings 50 may provide a reference for threading the catheter 22 into the vein. In some embodiments, the second plurality of markings 50 may provide a reference for determining whether the catheter 22 has become dislodged. In some embodiments, the first plurality of markings 48 may be spaced apart from each other such that the first distance 52 is half the length of the needle bevel. In some embodiments, the first distance 52 may be the catheter lie distance. In some embodiments, the first distance 52 may be the length of the catheter taper 58. In some embodiments, the second plurality of markings 50 may be located at a distance about 1/10 of the length of the catheter 22 measured from the catheter proximal end 26.

Figure 5:
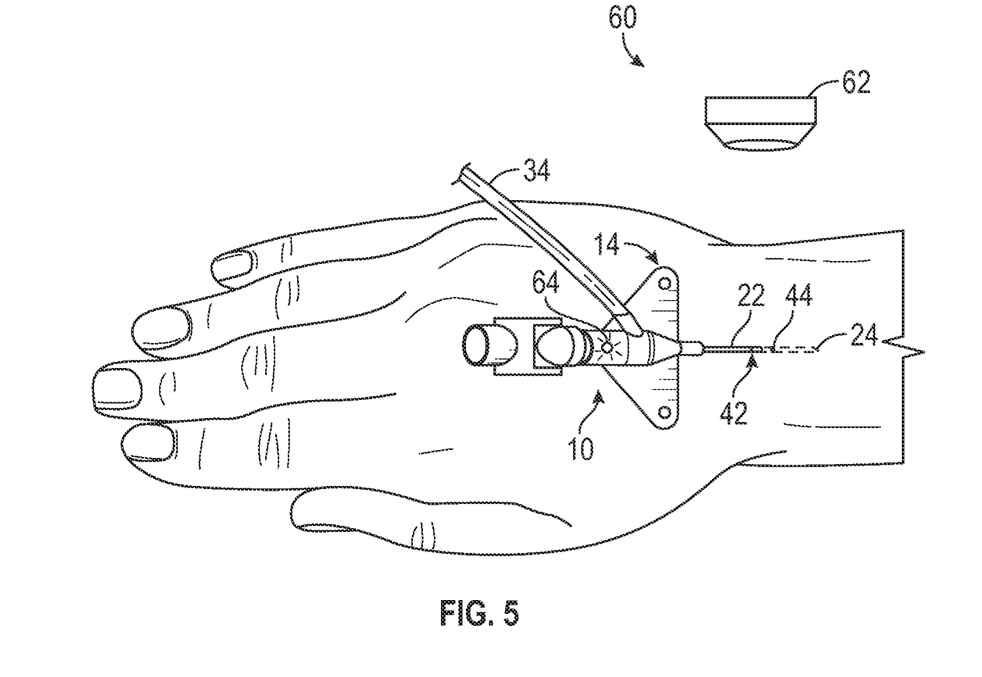
FIG. 5 is an upper perspective view of the catheter assembly of FIG. 1A disposed in a vasculature according to some embodiments.

Referring now to FIG. 5, in some embodiments, the position indicator 42 may indicate catheter dislodgement. In some embodiments, catheter dislodgement may be indicated by an exposed marking 44 that was not previously visible. In other embodiments, catheter dislodgement may be indicated by variation in the location of the marking 44 relative to the surface of skin. For example, after the clinician advances the catheter 22 several markings 44 within the vein prior to threading off the catheter 22 from the introducer needle 30, the marking 44 visible at the surface of the skin may be noted in the medical record, on the catheter assembly 14, or in other suitable location. In some embodiments, the notation may indicate the marking 44 by color band visible at the surface of or under the skin, a particular tick mark, a reference location, or a count of the number of markings 44 exposed.

In one example, a catheter 22 may include two markings 44 located near the proximal end 26 of the catheter 21. In some embodiments, the catheter 22 may be inserted into the vein and secured such that one of the markings 44 is exposed while another marking 44 is under the surface of the skin. In some embodiments, if both markings 44 are exposed, the clinician may be alerted to possible dislodgement and may conduct further investigation to determine an appropriate response.

Some embodiments may include a method for detecting catheter position. In some embodiments, the method may include providing a catheter assembly to introduce a catheter into a vasculature of a patient. Some embodiments of the catheter assembly may include a catheter adapter comprising a proximal end, a distal end, and a lumen extending therebetween. The catheter may extend from the distal end. In some embodiments, the catheter may include a proximal end, a tip, and a length of tubing therebetween. Some embodiments of the length of tubing may include a position indicator to indicate a position of the catheter relative to the vasculature.

In some embodiments, an introducer needle may extend through the length of tubing. Some embodiments of the introducer needle may include a sharp distal tip to introduce the catheter into the vasculature at an intravenous entry site of the patient. In some embodiments, the catheter may be secured such that the position indicator is aligned with the intravenous entry site. Some embodiments of the method may further include automatically monitoring a location of the position indicator relative to the intravenous entry site to detect catheter dislodgement.

In some embodiments, the position indicator may include a plurality of markings printed onto an outer surface of the length of tubing. In some embodiments, the method may further include automatically activating an alert in response to the location of the position indicator misaligning with the intravenous entry site.

Some embodiments may include a method to detect catheter 22 position. The method may include providing the catheter assembly 14 to introduce the catheter 22 into the vasculature. In some embodiments, the catheter assembly 14 may include a catheter adapter 16 comprising the proximal end 20, the distal end 18, and the lumen 21 extending therebetween. In some embodiments, the catheter 22 may extend from the distal end 18. The catheter 22 may include the proximal end 26, the tip 24, and the length of tubing therebetween. In some embodiments, the length of tubing may include the position indicator 42, which may indicate a depth of insertion of the catheter 22 into the vasculature or vein.

In some embodiments, the position indicator may include a marking 44 disposed on an outer surface of the length of tubing of the catheter 22. In some embodiments, an introducer needle 30 may extend through the length of tubing. Some embodiments of the introducer needle 30 may include a sharp distal tip 40 to introduce the catheter 22 into the vasculature at an intravenous entry site of the patient. In some embodiments, the catheter 22 may be advanced into the vasculature and secured such that the position indicator 42 is aligned with the intravenous entry site. In some embodiments, the catheter 22 may be advanced into the vasculature by several markings 44 before threading off the catheter 22 from the introducer needle 30.

In some embodiments, the catheter 22 may be inserted such that a first plurality of markings 48 is positioned within the vasculature and a second plurality of markings 50 is aligned or even with an outer surface of skin of the patient. In some embodiments, in response to a second of the markings 50 being aligned with the outer surface of the skin of the patient, the catheter 22 may be inserted to a second depth which may correspond to full insertion of the catheter 22 within the vein. In some embodiments, the second plurality of markings 50 may be proximal to the surface of skin of the patient. In some embodiments, the position indicator 42 may include a plurality of markings 44 spaced approximately 2-3 mm apart located at a distance about ⅒ of the catheter 22 length from the proximal end.

In some embodiments, the catheter adapter 14 may be secured to the patient. In some embodiments, variation in a position of one or more markings 44 relative to the surface of skin may indicate a potential catheter dislodgement. In this manner, some embodiments may facilitate early detection of catheter 22 dislodgment and enable corrective action to be taken.

Some embodiments of the method may further include automatically monitoring a location of the position indicator 42 relative to the intravenous entry site to detect catheter 22 dislodgement. In some embodiments, an image processor 62 or other device 60 may automatically monitor the location of the position indicator 42 relative to the catheter insertion site. In some embodiments, the image processor may be coupled to the proximal end 20 of the catheter adapter 16 and/or secured to the patient.

In some embodiments, the image processor 62 may be configured to record one or more images of the insertion site relative to the markings 44. In some embodiments, the image processor may also be configured to analyze the relative locations of the catheter 22 and/or the markings 44 to detect dislodgement of the catheter 22 and automatically activate an alert.

In some embodiments, the image processor 62 may detect the marking 44 and capture the image by any suitable means. In some embodiments, the image processor 62 may be configured to detect color contrast of the exposed markings 44. Embodiments of the image processor 62 may be combined with any other embodiments disclosed herein to facilitate placement of the catheter 22 within the vasculature and/or detection of catheter 22 dislodgement.

In some embodiments, in response to a determination that the catheter 22 has been dislodged, an alert 64 may be activated. In some embodiments, the alert may be located on the image processor 62 or any other suitable device 60. In some embodiments, in response to the tip 24 of the catheter 22 being dislodged or fully or partially withdrawn, or in response to the position indicator 42 misaligning with the intravenous entry site, the alert 64 may be automatically activated. In some embodiments, the alert 64 may be activated locally or remotely. In some embodiments, the alert 64 may include a visual, haptic, and/or audible alert. In some embodiments, one or more alerts 64 may change or stop in response the introducer needle 30 being removed from the vein, the catheter 22 or catheter tip 24 being removed from the vein, or the catheter 22 being at least partially withdrawn from the vein.

All examples and conditional language recited herein are intended for pedagogical objects to aid the reader in understanding the present disclosure and the concepts contributed by the inventor to furthering the art and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. An over-the-needle peripheral intravenous catheter assembly, comprising:
   a catheter adapter comprising a proximal end, a distal end, and a lumen extending therebetween;
   an over-the-needle peripheral intravenous catheter extending from the distal end of the catheter adapter, the over-the-needle peripheral intravenous catheter comprising a proximal end, a tip, and a length of tubing therebetween, wherein the length of tubing comprises at least one position indicator to indicate a position of the over-the-needle peripheral intravenous catheter relative to a vasculature, wherein the at least one position indicator comprises a first pair of markings and a second pair of markings, wherein the first pair of markings is disposed on an outer surface of the length of tubing closer to the tip of the over-the-needle peripheral intravenous catheter than the distal end of the catheter adapter, wherein the second pair of markings is disposed on the outer surface of the length of tubing closer to the distal end of the catheter adapter than the tip of the over-the-needle peripheral intravenous catheter, wherein a first marking and a second marking of the first pair of markings are spaced apart, wherein a first marking and a second marking of the second pair of markings are spaced apart, wherein the first pair of markings provides a reference for depth of insertion of the over-the-needle peripheral intravenous catheter and the second pair of markings provides an indicator of catheter dislodgement by variation in a location of the first marking or the second marking of the second pair of markings with respect to skin of a patient, wherein an unmarked portion of the tubing extends from the first pair of markings to the second pair of markings; and
   an introducer needle extending through the length of tubing of the over-the-needle peripheral intravenous catheter and comprising a sharp distal tip configured to introduce the over-the-needle peripheral intravenous catheter into the vasculature, wherein a distance between the first marking and the second marking of the first pair of markings is a lie distance, wherein the lie distance equals a distance between a proximal end of a bevel of the introducer needle and the tip of the over-the-needle peripheral intravenous catheter.

2. The over-the-needle peripheral intravenous catheter assembly of claim 1, wherein the first pair of markings or the second pair of markings is selected from the group consisting of colored bands, tick marks, and graduated marks.

3. The over-the-needle peripheral intravenous catheter assembly of claim 1, wherein the first pair of markings and the second pair of markings are uniformly spaced.

4. The over-the-needle peripheral intravenous catheter assembly of claim 1, wherein the second pair of markings is located at a distance from the proximal end of the catheter of about 1/10 of a length of the catheter.

5. The over-the-needle peripheral intravenous catheter assembly of claim 1, wherein a distance between the first marking and the second marking of the first pair of markings is half of a length of a bevel of the introducer needle.

6. The over-the-needle peripheral intravenous catheter assembly of claim 1, wherein the first pair of markings includes exactly two markings.

7. The over-the-needle peripheral intravenous catheter assembly of claim 1, wherein the first marking and the second marking of the first pair of markings are spaced apart by a length of a taper at the tip of the over-the-needle peripheral intravenous catheter.

8. The over-the-needle peripheral intravenous catheter assembly of claim 1, further comprising an image processor coupled to the over-the-needle peripheral intravenous catheter assembly, wherein the image processor is configured to record an image of an insertion site of the over-the-needle peripheral intravenous catheter assembly and analyze a location of the second pair of markings to detect dislodgement of the over-the-needle peripheral intravenous catheter.

9. The over-the-needle peripheral intravenous catheter assembly of claim 8, further comprising an alert, wherein in response to the image processor detecting the dislodgement, the alert is configured to be activated.

10. An over-the-needle peripheral intravenous catheter assembly, comprising:

an over-the-needle peripheral intravenous catheter comprising a proximal end, a tip, and a length of tubing therebetween; and an introducer needle extending through the over-the-needle peripheral intravenous catheter, wherein the introducer needle comprises a bevel;

a position indicator disposed on an outer surface of the length of tubing, the position indicator configured to indicate a position of the over-the-needle peripheral intravenous catheter within a vasculature, wherein the position indicator comprises a first pair of markings disposed closer to the tip of the over-the-needle peripheral intravenous catheter than the proximal end of the over-the-needle peripheral intravenous catheter, wherein the first pair of markings provides a reference for depth of insertion of the over-the-needle peripheral intravenous catheter into the vasculature, wherein a first marking and a second marking of the first pair of markings are spaced apart by a lie distance, wherein the lie distance is equal to a distance between a proximal end of the bevel and the tip of the over-the-needle peripheral intravenous catheter.

11. The over-the-needle peripheral intravenous catheter assembly of claim 10, wherein the position indicator is printed onto the outer surface of the length of tubing.

12. The over-the-needle peripheral intravenous catheter assembly of claim 10, wherein the first pair of markings is spaced apart by 2-3 mm.

13. The over-the-needle peripheral intravenous catheter assembly of claim 12, wherein the first pair of markings comprises a non-uniform characteristic selected from the group consisting of color, width, and length.

14. The over-the-needle peripheral intravenous catheter assembly of claim 10, wherein each of the first pair of markings is selected from the group consisting of colored bands, tick marks, and graduated marks.

* * * * *